United States Patent [19]

Jung et al.

[11] Patent Number: 5,412,093
[45] Date of Patent: May 2, 1995

[54] 3-HETEROCYCLIC THIOMETHYL CEPHALOSPORINS

[75] Inventors: Frederic H. Jung, Rillay la Montagne; Annie A. Olivier, Reims, both of France

[73] Assignee: ICI Pharma, Cergy Cedex, France

[21] Appl. No.: 111,402

[22] Filed: Aug. 25, 1993

Related U.S. Application Data

[62] Division of Ser. No. 740,420, Aug. 5, 1991, Pat. No. 5,262,410, which is a division of Ser. No. 133,482, Dec. 15, 1987, Pat. No. 5,057,511.

[30] Foreign Application Priority Data

Dec. 23, 1986 [EP] European Pat. Off. ........... 86402917

[51] Int. Cl.⁶ ......................................... C07D 501/18
[52] U.S. Cl. .................................. 540/221; 540/226; 540/222
[58] Field of Search .................. 540/222, 221, 226

[56] References Cited

U.S. PATENT DOCUMENTS

| | | | |
|---|---|---|---|
| 4,278,793 | 7/1981 | Durckheimer | 544/27 |
| 4,678,781 | 7/1987 | Jung | 540/222 |
| 4,758,556 | 7/1988 | Durckheimer et al. | 514/206 |
| 5,057,511 | 10/1991 | Jung et al. | 560/227 |
| 5,114,933 | 5/1992 | Bertrandrie et al. | 514/202 |
| 5,262,410 | 11/1993 | Jung et al. | 514/210 |

FOREIGN PATENT DOCUMENTS

| | | |
|---|---|---|
| 241901 | 10/1987 | European Pat. Off. . |
| 0241901 | 10/1987 | European Pat. Off. . |
| 2385722 | 10/1987 | France . |
| 1399086 | 6/1975 | United Kingdom . |
| 1496757 | 11/1978 | United Kingdom . |

OTHER PUBLICATIONS

Chemical Abstracts vol. 109:54525 (1988) copy not provided.
Chemical Abstracts vol. 108:75055 (1988) copy not provided.
Chemical Abstracts vol. 102:137797 (1985) copy not provided.
Chemical Abstracts vol. 90 186883(b) (1979).
Chemical Abstracts vol. 90 38940 (c) (1979).
Chemical Abstracts vol. 95 132023 (z) (1981).

*Primary Examiner*—Nicholas Rizzo
*Attorney, Agent, or Firm*—Cushman Darby & Cushman

[57] ABSTRACT

Cephalosporin compounds having a 3-position substituent of the formula (I) are described:

$$-CH_2-S-Q-(Y)_n-P$$

wherein Q is a 5- or 6-membered heterocyclic ring, P is a benzene ring substituted by groups $R^1$ and $R^2$ which are ortho with respect to one another, wherein $R^1$ is hydroxy or an in vivo hydrolysable ester thereof and $R^2$ is hydroxy, an in vivo hydrolysable ester thereof, carboxy, sulpho, hydroxymethyl, methanesulphonamido or ureidos; or P is a group of the formula (II) or (III):

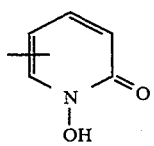

(II)

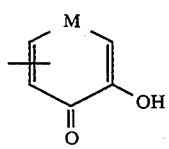

(III)

wherein M is oxygen or a group $NR^3$ wherein $R^3$ is hydrogen or $C_{1-4}$alkyl; said ring P being further optionally substituted; and $-(Y)_n-$ is a bond or various linking groups or $-(Y)-_n$ may be such so that rings Q and P are fused.

The use of such compounds as antibacterial agents is described as are processes for their preparation and intermediates therefor.

4 Claims, No Drawings

3-HETEROCYCLIC THIOMETHYL CEPHALOSPORINS

This is a division of application Ser. No. 07/740,420, filed Aug. 5, 1991, now U.S. Pat. No. 5,262,410, which is a division of appln. Ser. No. 07/133,482, filed Dec. 15, 1987, now U.S. Pat. No. 5,057,511.

The present invention relates to cephalosporins and in particular to such compounds comprising a catechol or related group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans. The compounds of this invention also have non-therapeutic uses as they can be used in conventional manner in industry for example they can be used as disinfectants and food preservatives. The compounds of this invention, however, are primarily of therapeutic interest as they show a desirable profile of activity and duration in their antibacterial effect.

Investigation into new cephalosporin derivatives has been intense over the past 25 years with many thousands of patents and scientific papers having been published. A particular problem associated with the commercially available cephalosporins is the lack of potency against strains of Pseudomonas. The present invention provides cephalosporin derivatives having novel 3-position substituents, which derivatives possess good antibacterial activity and in particular against strains of Pseudomonas.

U.S. Pat. No. 4,278,793 discloses cephalosporins having a 3-position substituent of the formula: $-CH_2Y$ wherein Y can be the residue of a nucleophilic compound, preferably a sulphur, nitrogen or oxygen nucleophilic compound. GB1496757 discloses cephalosporins having a 3-position substituent of the formula: $-CH_2Y$ wherein Y can be the residue of a nucleophilic compound; this specification includes a discussion of nitrogen, carbon, oxygen and sulphur nucleophiles. Many possible values of Y are mentioned. These specifications are typical of many specifications that describe cephalosporins having nucleophilic moities linked via a methylene group to the 3-position of a cephalosporin. However, although there has been intense research over a long period of time, there has been no teaching or suggestion of the compounds of the present invention. These contain specific ring systems that are characterised by having hydroxy groups or related substituents ortho to one another. These hitherto undisclosed ring systems give rise to particularly good activity against strains of Pseudomonas.

Accordingly the present invention provides a cephalosporin compound having a 3-position substituent of the formula (I):

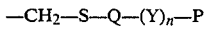

wherein Q represents a 5- or 6-membered heterocyclic ring containing 1-4 heteroatoms selected from oxygen, nitrogen and sulphur (optionally fused to a benzene ring or to a further such heterocyclic ring) wherein Q optionally, where possible, may bear a positive charge and may optionally be substituted on an available carbon or nitrogen atom by carboxy, sulpho, $C_{1-4}$ alkoxycarbonyl or $C_{1-4}$ alkyl (which alkyl group may itself optionally be substituted by carboxy, sulpho or $C_{1-4}$ alkoxycarbonyl);

P represents:

(i) a benzene ring (optionally fused to a further benzene ring (so forming a naphthyl group) or to a 5 or 6 membered heterocyclic aromatic group containing 1, 2 or 3 heteroatoms selected from nitrogen, oxygen and sulphur) said benzene ring (or in the case of naphthyl either benzene ring) substituted by groups $R^1$ and $R^2$ which are ortho with respect to one another wherein $R^1$ is hydroxy or an in vivo hydrolysable ester thereof and $R^2$ is hydroxy, an in vivo hydrolysable ester thereof, carboxy, sulpho, hydroxymethyl, methanesulphonamido or ureido;

(ii) a group of the formula (II):

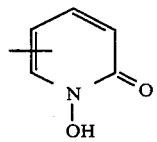

or (iii) a group of the formula (III):

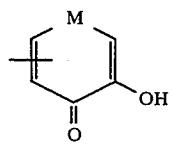

wherein M is oxygen or a group $NR^3$
wherein $R^3$ is hydrogen or $C_{1-4}$ alkyl:

ring P (or, in the case wherein ring P is a benzene ring and is fused to another benzene ring, either benzene ring) is optionally further substituted by $C_{1-4}$ alkyl, halo, hydroxy, hydroxy $C_{1-4}$ alkyl, cyano, trifluoromethyl, nitro, amino, $C_{1-4}$ alkylamino, di-$C_{1-4}$ alkylamino, amino $C_{1-4}$ alkyl, $C_{1-4}$ alkylamino $C_{1-4}$ alkyl, di-$C_{1-4}$ alkylamino $C_{1-4}$ alkyl, $C_{1-4}$ alkanoyl, $C_{1-4}$ alkoxy, $C_{1-4}$ alkylthio, $C_{1-4}$ alkanoyloxy, carbamoyl, $C_{1-4}$ alkylcarbamoyl, di-$C_{1-4}$ alkyl carbamoyl, carboxy, carboxy $C_{1-4}$ alkyl, sulpho, sulpho $C_{1-4}$ alkyl, $C_{1-4}$ alkanesulphonamido, $C_{1-4}$ alkoxycarbonyl, $C_{1-4}$ alkanoylamino, nitroso, thioureido, amidino, ammonium, mono-, di- or tri-$C_{1-4}$ alkylammonium pyridinium, or a 5-membered heterocyclic ring containing 1 to 4 heteroatoms selected from oxygen, nitrogen and sulphur which is optionally substituted by 1, 2 or 3 $C_{1-4}$ alkyl or $C_{1-4}$ alkoxy groups, n=0 or 1 such that when n=1 Y represents a covalent bond between Q and P or a $C_{1-4}$ alkylene group optionally substituted by carboxy or sulpho or Y represents a group $-(CH_2)_m-Y'-$ wherein m=1 or 2 and Y' is $-O.CO-$ or $-NH.CO-$; and when n=0 Q and P both represent monocyclic rings which are fused on an available carbon—carbon or carbon—nitrogen bond.

In one particular aspect $-(Y)_n-$ is $C_{1-4}$ alkylene optionally substituted by carboxy. In another particular aspect $-(Y)_n-$ is a covalent bond directly linking groups Q and P. In yet another aspect $-(Y)_n-$ is such that rings Q and P are fused to form a bicyclic ring system. In a preferred aspect Y is a covalent bond or a methylene or ethylene linkage.

In one aspect ring P is a benzene ring substituted by groups R¹ and R² as hereinbefore defined. R¹ is hydroxy or an in vivo hydrolysable ester thereof. In vivo hydrolysable esters are those pharmaceutically acceptable esters that hydrolyse in the human or animal body to produce the parent hydroxy compound. Such esters can be identified by administering, e.g. intravenously to a test animal, the compound under test and subsequently examining the test animal's body fluids. Suitable in vivo hydrolysable esters include $C_{1-6}$ alkanoyloxy for example acetoxy, propionyloxy, pivaloyloxy, $C_{1-4}$ alkoxycarbonyloxy for example ethoxycarbonyloxy, phenylacetoxy and phthalidyl.

Conveniently both R¹ and R² have the same value and are both hydroxy or are both in vivo hydrolysable esters, for example they are both acetoxy or both pivaloyloxy.

In a preferred aspect P is a benzene ring optionally fused to another benzene ring so forming a naphthyl group. As stated hereinbefore either benzene group may be substituted by R¹ and R² and by other optional substituents. Particular optional substituents are $C_{1-4}$ alkyl for example methyl, ethyl or isopropyl, halo for example chloro, bromo or fluoro, hydroxy, hydroxy $C_{1-4}$ alkyl for example hydroxymethyl, amino, nitro, $C_{1-4}$ alkoxy for example methoxy or ethoxy, carboxy $C_{1-4}$ alkyl for example carboxymethyl, $C_{1-4}$ alkanoylamino for example acetamido, trifluoromethyl, carboxy, carbamoyl, cyano, sulpho, $C_{1-4}$ alkanesulphonamido for example methanesulphonamido, $C_{1-4}$ alkanoyl for example acetyl, $C_{1-4}$ alkanoyloxy for example acetoxy or propionoxy and $C_{1-4}$ alkoxycarbonyl for example methoxycarbonyl. Of these, favoured substituents are sulpho, carboxymethyl, methyl, ethyl, methoxy, bromo, chloro, fluoro and nitro.

The skilled man will realise that when P is a benzene ring up to 3 optional substituents are possible; when a naphthyl ring is formed more substituents are possible and up to 2 or 3 substituents are possible with the rings of formulae (II) and (III). In general, we prefer up to 2 optional substituents, which may be the same or different.

Particular meanings for ring Q when it is a 5-membered ring are pyrazole, imidazole, thiazole, isothiazole, thiadiazole, triazole and tetrazole. In one aspect Q is imidazole, pyrazole, isothiazole, triazole or tetrazole. In another aspect Q is thiadiazole or thiazole wherein Y is A $C_{1-4}$ alkylene group optionally substituted by carboxy or sulpho or Y represents a group —($CH_2$)$_m$—Y'— as defined hereinbefore.

In a further aspect ring Q is a 6-membered ring for example pyridine, pyridazine, pyrimidine and pyrazine, in which n=1 and Y may be linked to a carbon atom of Q or to a nitrogen atom, or n=0 and the rings Q and P are fused. When Y is linked to a carbon atom of Q, or when Q and P are fused, Q may be uncharged, or may bear a positive charge for example when a nitrogen atom of Q is substituted, for example by a $C_{1-4}$ alkyl group eg a methyl group. When Y is linked to a nitrogen atom of such a group Q then Q will bear a positive charge.

Particular meanings for —S—Q— are rings having the structures set out in formulae VI–XII:

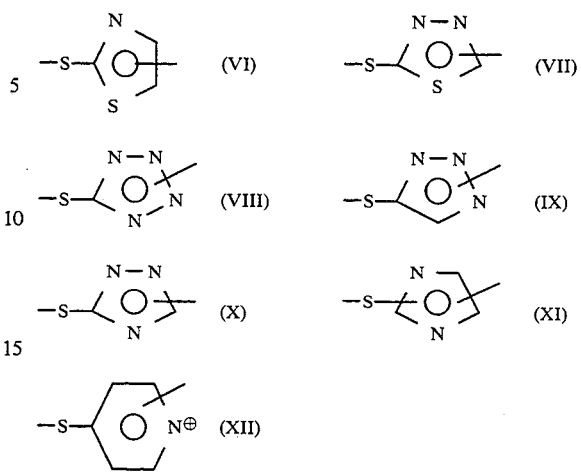

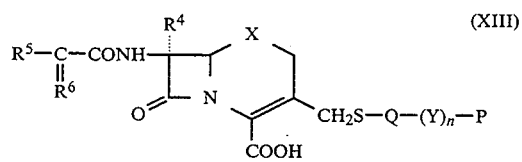

As stated hereinabove the present invention relates to cephalosporins having a novel 3-position substituent. A particular class of cephalosporins within the present invention is that of the formula (XIII):

$$R^5-\underset{R^6}{\overset{R^4}{\underset{\|}{C}}}-CONH-\left[\begin{array}{c}X\\\\N\end{array}\right]-CH_2S-Q-(Y)_n-P$$
$$\text{COOH}$$
(XIII)

and salts and esters thereof wherein Q, Y, P and n are as hereinbefore defined;

X is sulphur, oxygen, methylene or sulphinyl;

R⁴ is hydrogen, methoxy or formamido; and R⁵ and R⁶ are groups known for such positions in the cephalosporin art.

Preferably X is sulphur.

Preferably R⁴ is hydrogen.

R⁵ is for example 2-aminothiazol-4-yl or 2-aminooxazol-4-yl each optionally substituted in the 5-position by fluorine, chlorine or bromine, or R⁵ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R₆ is for example of the formula =N.O.R⁷ (having the syn configuration about the double bond) wherein R⁷ is hydrogen, (1-6C)alkyl, (3-8C)cycloalkyl, (1-3C)alkyl(3-6C)cycloalkyl, (3-6C)cycloalkyl(1-3C)alkyl, (3-6C)alkenyl, optionally substituted by carboxy, (5-8C)cycloalkenyl, (3-6C)alkynyl, (2-5C)alkylcarbamoyl, phenylcarbamoyl, benzylcarbamoyl, (1-4C)alkylcarbamoyl(1-4C)alkyl, di(1-4C)alkylcarbamoyl(-1-4C)alkyl, (1-4C)haloalkylcarbamoyl(1-4C)alkyl, (1-3C)haloalkyl, (2-6C)hydroxyalkyl, (1-4C)alkoxy(-2-4C)alkyl, (1-4C)alkylthio(2-4C)alkyl, (1-4C)alkanesulphinyl(1-4C)alkyl, (1-4C)alkanesulphonyl(1-4C)alkyl, (2-6C)aminoalkyl, (1-4C)alkylamino(1-6C)alkyl, (2-8C)dialkylamino(2-6C)alkyl, (1-5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or R⁷ is of the formula XIV:

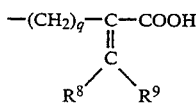

$$-(CH_2)_q-\underset{\underset{R^9}{R^8}}{\overset{\overset{\|}{C}}{C}}-COOH \qquad (XIV)$$

wherein q is one or two and $R^8$ and $R^9$ are independently hydrogen or $C_{1-4}$ alkyl; or $R^7$ is of the formula XV:

$$-CR^{10}R^{11}-(CH_2)_r-COR^{12} \qquad XV$$

wherein r is 0-3, $R^{10}$ is hydrogen, (1-3C)alkyl or methylthio, $R^{11}$ is hydrogen (1-3C)alkyl, (3-7C)cycloalkyl, cyano, carboxy, (2-5C)carboxyalkyl or methanesulphonylamino, or $R^{10}$ and $R^{11}$ are joined to form, together with the carbon to which they are attached, a (3-7C)carbocyclic ring, and $R^{12}$ is hydroxy, amino, (1-4C)alkoxy, (1-4C) alkylamino or of the formula $NHOR^{13}$ in which $R^{13}$ is hydrogen or (1-4C)alkyl;

or $R^6$ may be of the formula $=CH.R^{14}$ wherein $R^{14}$ is hydrogen, halogen, (1-6C)alkyl, (3-7C)cycloalkyl, (2-6C)alkenyl, (3-7C)cycloalkenyl, phenyl or benzyl.

Particular meanings for $R^7$ are hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, 2-chloroethyl, 2-fluoroethyl, 2-bromoethyl, 2-hydroxyethyl, 3-hydroxypropyl, 2-methoxyethyl, 2-ethoxyethyl, 2-methylthio-ethyl, 2-methanesulphinylethyl, 2-methanesulphonyl-ethyl, 2-aminoethyl, 3-aminopropyl, 2-methylamino ethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)-ethyl, tetrahydropyran-2-yl, thietan-3-yl, 2-oxopyrrolidinyl and 2-oxotetrahydrofuran-3-yl, or, when $R^7$ is of the formula XIV in which q is 1 or 2, a particular meaning for $R^7$ is when $R^8$ and $R^9$ are hydrogen or methyl, or, when $R^7$ is of the formula XV, a particular meaning for $R^7$ is when r=0 and $R^{10}$ is hydrogen, methyl or methylthio, $R^{11}$ is hydrogen, methyl, cyclopropyl, cyclobutyl, cyclopentyl, cyclohexyl, cyano, carboxy, carboxymethyl, 2-carboxyethyl or methanesulphonylamino, or when $R^{10}$ and $R^{11}$ are joined to form, together with the carbon to which they are attached, a cyclopropane, cyclobutane, cyclopentane, cyclohexane or cycloheptane ring and $R^{12}$ is hydroxy, amino, methoxy, ethoxy, methylamino, ethylamino, or of the formula $NHOR^{13}$ in which $R^{13}$ is hydrogen, methyl or ethyl.

Preferably $R^7$ is $C_{1-6}$ alkyl for example methyl or ethyl, 1-carboxycyclobutyl, 1-carboxycyclopentyl, or 2-carboxyprop-2-yl. In particular $R^7$ is 2-carboxyprop-2-yl.

Particular meanings for $R^{14}$ are hydrogen, methyl, ethyl or chlorine.

The cephalosporin derivatives referred to herein are generally named in accordance with the 'cephem' nomenclature and numbering system proposed in J.A.C.S. 1962, 84, 3400.

It will be realised, of course, that the present invention covers all isomeric and tautomeric forms of the aforementioned compounds. For example the rings of the formula (III) may be in pyranone or hydroxypyridine form.

As stated hereinbefore the compounds of this invention ar primarily intended for use in therapy. Therefore in a preferred aspect the present invention provides a cephalosporin compound having a 3-position substituent of the formula I or a pharmaceutically acceptable salt or ester thereof. Suitable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, or N,N-dibenzylethylamine.

In order to use a compound of the present invention or a pharmaceutically acceptable salt or ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a cephalosporin compound having a 3-position substituent of the formula I or a pharmaceutically acceptable salt or ester thereof and a pharmaceutically acceptable carrier.

The pharmaceutical compositions of this invention may be administered in standard manner for the disease condition that it is desired to treat, for example by oral, rectal or parenteral administration. For these purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the pharmaceutically acceptable cephalosporin derivative of the present invention the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 50% w/w of the cephalosporin derivative, or one suitable for oral administration in unit dosage form, for example a tablet or capsule which contains between 100 mg. and 1 g. of the cephalosporin derivative.

The pharmaceutical compositions of the invention will normally be administered to man in order to combat infections caused by bacteria, in the same general manner as that employed for cephalothin, cefoxitin, cephradine, ceftazidime and other known clinically used cephalosporin derivatives; due allowance being made in terms of dose levels for the potency of the cephalosporin derivative of the present invention relative to the known clinically used cephalosporins. Thus each patient will receive a daily intravenous, subcutaneous or intramuscular dose of 0.05 to 30 g., and preferably 0.1 to 10 g., of the cephalosporin derivative, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

In a further aspect the present invention provides a process for preparing a cephalosporin compound having a 3-position substituent of the formula I, which process comprises:

(a) reacting a cephalosporin compound having a 3-position substituent of the formula: —CH$_2$L wherein L is a leaving group, with a source of —S—Q—(Y)$_n$—P wherein Y, Q, P and n are as hereinbefore defined;

(b) reacting a cephalosporin compound having a 3-position substituent of the formula, —CH$_2$SH with a source of —Q—(Y)$_n$—P wherein Q, Y, P and n are as hereinbefore defined;

(c) reacting a cephalosporin compound having a 3-position substituent of the formula —CH$_2$—S—Q—J with a compound of the formula K—P wherein J and K are such that the reaction takes place to form the link —(Y)$_n$— between Q and P; or (d) for preparing compounds of the formula (XIII), reacting a compound of the formula (XVI) with a compound of the formula (XVII) or a reactive derivative thereof:

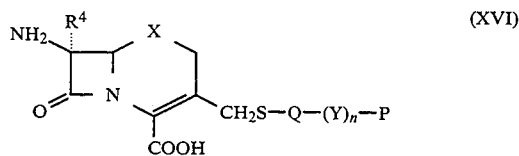

(XVI)

(XVII)

wherein R$^4$, R$^5$, R$^6$, X, Y, Q, P and n are as hereinbefore defined; or e) for compounds of the formula (XIII) wherein R$^6$ is a group =NOR$^7$, reacting a compound of the formula (XVIII):

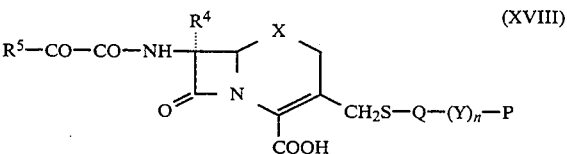

(XVIII)

wherein R$^4$, R$^5$, X, Y, Q, P and n are as hereinbefore defined, with a compound of the formula: R$^7$ONH$_2$ wherein R$^7$ is as hereinbefore defined; or f) for compounds of the formula (XIII) wherein R$^6$ is a group =NOR$^7$ and R$^7$ is other than hydrogen, reacting a compound of the formula (XIII) as hereinbefore defined wherein R$^6$ is a group =NOH with a compound of the formula (XIX):

(XIX)

wherein L$^1$ is a leaving group and R$^{15}$ is a group R$^7$ other than hydrogen; or g) for compounds of the formula (XIII) forming a group R$^5$ by cyclising an appropriate precursor thereof:

wherein any functional groups are optionally protected: and thereafter, if necessary:

i) removing any protecting group, ii) for preparing in vivo hydrolysable esters, esterifying corresponding hydroxy groups, iii) converting compounds wherein X is S to compounds wherein X is sulphinyl and vice versa, iv) forming a pharmaceutically acceptable salt.

In the reaction between a cephalosporin compound having a 3-position substituent of the formula: —CH$_2$L and a source of —S—Q—(Y)$_n$—P, conveniently L is a leaving group such as halo for example iodo, bromo or chloro, or is C$_{1-4}$ alkanoyloxy for example acetoxy. Typically a source of —S—Q—(Y)$_n$—P is the mercapto derivative HS—Q—(Y)$_n$—P. Such compounds are either known or are prepared in conventional manner by known methods as will be apparent to the skilled man. In particular reference should be made to the established techniques of displacing leaving groups at the 3'-position of cephalosporin derivatives by a wide variety of sulphur nucleophiles. In a similar manner a cephalosporin compound having a 3-position substituent of the formula —CH$_2$SH is reacted with a source of —Q—(Y)$_n$—P, for example L'—Q—(Y)$_n$—P wherein L' is a leaving group.

The cephalosporin starting materials for these reactions are known from the art, or are made by methods analogous thereto. See for example EP-A-127992 and EP-A-164944.

The reaction between compounds of the formulae (XVI) and (XVII) is performed under conditions conventional in the cephalosporin art, for example under standard acylation conditions wherein for example the acid is activated as an acid bromide, acid chloride, anhydride or activated ester, or the reaction is performed in the presence of a coupling reagent such as dicyclohexylcarbodi-imide.

The compounds of the formula (XVI) can be prepared in a manner analogous to that described for the compounds of the formula (I), with the 7-amino group being optionally protected.

The reaction between compounds of the formula (XVIII) and R$^7$ONH$_2$ is performed under conditions standard in the general chemical and/or cephalosporin art. The compounds of the formula (XVIII) can be prepared in a manner analogous to that described for the compounds of the formula (I).

The reaction between the compound of the formula (XIII) wherein R$^6$ is a group =NOH and a compound of the formula (XIX) is performed under conditions standard in the general chemical and/or cephalosporin art.

A group R$^5$ may be formed by cyclizing an appropriate precursor. For example compounds of the formulae (XX) and (XXI):

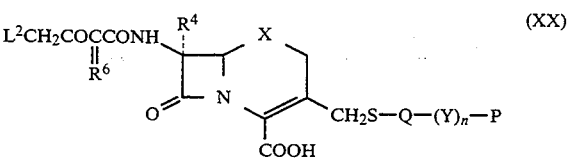

(XX)

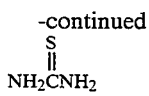

(XXI)

wherein $R^4$, $R^6$, X, Y, Q, P and n are as hereinbefore defined and $L^2$ is a leaving group, may be reacted to form a 2-aminothiazol-4-yl group. A nitrogen atom of the thiourea may be optionally protected during this cyclization.

The compounds of the formula (XX) can be prepared in a manner analogous to that described for the compounds of the formula I.

The compounds of the formulae (XVII), (XIX) and $R^7ONH_2$ are known from, or can be made by the methods of, the general chemical and/or cephalosporin art.

The compounds of the formulae (XVI), (XVIII) and (XX) are novel and as such form a further aspect of the present invention.

In the process of this invention any functional group can be optionally protected, if appropriate. Such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming phenol, silanol or stannanol (the said alcohol, phenol, silanol or stannanol preferably containing 1-20 carbon atoms).

Examples of carboxyl protecting groups include straight or branched chain (1-12C)alkyl groups (eg isopropyl, t-butyl); halo lower alkyl groups (eg 2-iodoethyl, 2,2,2-trichloroethyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxy-carbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2-6C)alkenyl groups (eg allyl and vinylethyl).

Methods particularly appropriate for the removal of carboxyl protecting groups include for example acid-, base-, metal- or enzymically-catalysed hydrolysis.

Examples of hydroxyl protecting groups include lower alkanoyl groups (eg acetyl); lower alkoxycarbonyl groups (eg t-butoxycarbonyl); halo lower alkoxycarbonyl groups (eg 2-iodoethoxycarbonyl, 2,2,2-trichloroethoxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups. In addition two hydroxy groups substituted on adjacent carbon atoms, for example in the catechol moiety, may be protected in the form of a cyclic acetal such as the methylenedioxy moiety.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; acyl (eg alkoxycarbonyl and aralkoxycarbonyl eg t-butoxycarbonyl and benzyloxycarbonyl); trialkylsilyl (eg trimethylsilyl and t-butyldimethylsilyl); alkylidene (eg methylidene); benzylidene and substituted benzylidene groups, and the phthalimido group.

Esterification of hydroxy groups (ie $R^1$ and $R^2$) to form in vivo hydrolysable esters is performed in conventional manner. Reduction of a cephalosporin sulphoxide to a cephalosporin and oxidation of a sulphide to a sulphoxide are performed according to methods known in the art.

The following biological test methods, data and Examples serve to illustrate this invention.

ANTIBACTERIAL ACTIVITY

The pharmaceutically acceptable cephalosporin compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. The compounds have particularly high activity in vitro against strains of *Pseudomonas aeruginosa*.

The antibacterial properties of the compounds of the invention may also be demonstrated in vivo in conventional mouse protection tests.

Cephalosporin derivatives have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Isosensitest agar medium. The antibacterial activity is described in terms of the minimum inhibitory concentration (M1C) determined by the agar-dilution technique with an inoculum size of $10^4$ CFU/spot.

| ORGANISM | MIC ($\mu l/ml$) EXAMPLE | | |
|---|---|---|---|
|  | 1 | 5 | 9 |
| P. aeruginosa PU21 (A8101028) | 0.06 | 0.25 | 0.125 |
| Ent. cloacae P99 (A8401054) | 0.125 | 0.03 | 1 |

-continued

| ORGANISM | MIC (μl/ml) EXAMPLE | | |
| --- | --- | --- | --- |
| | 1 | 5 | 9 |
| Serr. marcesens (A9421003) | 0.03 | 0.015 | 0.25 |
| Pr. morganii (A8433001) | 0.03 | 0.125 | 0.5 |
| Kleb. aerogenes (A8391027) | 0.015 | 0.008 | 0.125 |
| E. coli DCO (A8341098) | 0.008 | 0.008 | 0.03 |
| St. aureus 147N (A8601052) | 4 | 2 | >128 |
| S. dublin (A8369001) | 0.03 | 0.008 | 0.125 |
| Strep. pyogenes (A681018) | — | 0.03 | 0.5 |

In the following Examples the following abbreviations are used:
7-ACA=7-aminocephalosporanic acid
AcOH=acetic acid
BSA=bistrimethylsilylacetamide
DMF=dimethylformamide
DMSO=dimethylsulphoxide
EtOH=ethanol
HPLC=high pressure liquid chromatography
MeOH=methanol
TEA=triethylamine
TFA=trifluoroacetic acid The NMR spectra are taken at 90 MHz and are quoted in terms of delta values in parts per million (ppm) with reference to tetramethylsilane (delta=0). The solvent used was $DMSOd_6/CD_3COOD/TFA$ except where otherwise indicated. In the quotation of NMR data s=singlet, d=doublet, t=triplet, q=quartet, m=multiplet, br=broad.

EXAMPLE 1

7-[2-(2-Aminothiazol-4-yl)-2-((Z)-1-carboxy-1-methylethoxyimino) acetamido]-3-[2-(3,4-dihydroxyphenyl)-1,3,4-thiadiazol-5-ylthiomethyl]ceph-3-em-4-carboxylic acid (a) Methyl 3,4-dihydroxybenzoate (6 g) was heated with hydrazine hydrate (3.4 ml) at 110° C. with stirring for 15 minutes. The solid formed on cooling was triturated with ethanol and the crystals filtered to yield 5 g (83%) of the hydrazide of 3,4-dihydroxybenzoic acid, NMR ($DMSO_{d6}$+AcOD): 6.7 (d,1H); 7.2 (dd,1H); 7.3 (d,1H).

(b) To the product from (a) above (4.5 g) in absolute ethanol was added KOH (5.6 g) and carbon disulphide (2.4 ml). Stirring was continued for 20 hours. The solvents were evaporated, and the crude product (9 g potassium 3,4-dihydroxy-benzoyldithiocarbazate) used in the next step.

(c) The product of (b) above was added in small portions, with stirring, to conc. $H_2SO_4$ (40 ml) cooled below 5° C., over 30 minutes. The crude product was poured on to crushed ice and the precipitate filtered and washed with water. It was then dissolved in ether and washed to neutrality with water. The ether was evaporated and the solid dissolved in dichloromethane, insoluble material was filtered off after evaporation of dichloromethane and 2-mercapto-5-(3,4-dihydroxyphenyl)-1,3,4-thiadiazole (1.2 g) obtained, NMR ($DMSO_{d6}$, AcOD, TFA): 6.84 (d,1H); 7.04 (dd,1H); 7.15 (d,1H).

(d) 7-[2-(2-Aminothiazol-4-yl)-2-((Z)-1-carboxy-1-methylethoxyimino)acetamido]-3-acetoxymethylceph-3-em-4-carboxylic acid (527 mg), the product of (c) above (270 mg) and sodium iodide (1.5 g) in 5 ml water at pH 6.5–7 were heated at 65° C. for 5.5 hours. The pH was maintained at 7 by the addition of AcOH or $NaHCO_3$ during the reaction, which was followed by HPLC. When reaction was complete, the solvent was evaporated and the crude product purified by preparative HPLC eluting with MeOH/$(NH_4)_2CO_3$ buffer 30/70 to yield the title compound (58 mg), NMR ($DMSO_{d6}$, AcOD, TFA): 1.56 (s,6H); 3.7 (m,2H); 4.4 (m,2H); 5.2 (d,1H); 5.9 (d,1H); 6.85 (d,1H); 7.05 (s,1H); 7.1 (dd,1H); 7.35 (d,1H).

EXAMPLE 2

7-[2-(2-Aminothiazol-4-yl)-2-((Z)-ethoxyimino)acetamido]-3-[2-(3,4-dihydroxyphenyl)-1,3,4-thiadiazol-5-ylthiomethyl]ceph-3-em-4-carboxylic acid 1 equivalent of 7-amino-3-[2-(3,4-dihydroxyphenyl)-1,3,4-thiadiazol-5-ylthiomethyl]ceph-3-em-4-carboxylic acid was silylated with 4 equivalents of bistrimethylsilylacetamide in anhydrous dichloromethane at room temperature for three hours. To this solution, cooled to 0° C. under argon, was added 1 equivalent of 2-[(Z)-ethoxyimino-2-(tritylaminothiazol-4-yl) acetic acid chloride (prepared from the corresponding acid (1 equivalent), 1 equivalent $PCl_5$ and 1 equivalent TEA in dichloromethane at 0° C. for 2 hours followed by evaporation of the solvent and all $POCl_3$, and redissolution in dichloromethane). After a few minutes at 0° C., the solvent was evaporated, and all the protecting groups removed by treating the crude reaction mixture with TFA/water for 1 hour at room temperature. The solvents were evaporated and the crude product dissolved in MeOH and precipitated in ether. Further purification was achieved by MPLC, to yield the title compound (7%), NMR ($DMSO_{d6}$, AcOD, TFA), 1.25 (t,3H); 3.7 (m,2H); 4.2 and 4.25 (2d,2H); 4.4 (q,2H); 5.15 (d,1H); 5.75 (d,1H); 6.85 (d,1H); 7 (s,1H); 7.15 (d,1H); 7.3 (s,1H).

EXAMPLE 3

7-[1-(2-Aminothiazol-4-yl)-1-(Z)-propenecarboxamido]-3-[(2-(3,4-dihydroxyphenyl)-1,3,4-thiadiazol-5-ylthiomethyl]ceph-3-em-4-carboxylic acid To a solution of (Z)-1-(2-aminothiazol-4-yl)-propene-1-carboxylic acid (370 mg, 2 mmol) (prepared as described in European Patent Application No. 0107138) and N-ethyl-diisopropylamine (380 μl, 2.2 mmol) in DMF (3 ml) at −50° C. was added methylsulphonyl chloride ($CH_3SO_2Cl$) (170 μl, 2 mmol). The mixture was stirred for 1 hour at −50° C. The solution was then added rapidly to a cold (0° C.) solution of 7-amino-3-[(2-(3,4-dihydroxyphenyl)-1,3,4-thiadiazol-5-ylthiomethyl]ceph-3-em-4-carboxylic acid (300 mg, 2 mmol) and TEA (560 μl, 4 mmol in 2 ml DMF and 0.5 ml water). Stirring was continued at room temperature for 30 minutes. The solvents were evaporated and the product purified by preparative HPLC, eluting with MeOH/$(NH_4)_2CO_3$ buffer 30/70 to yield the title compound (50 mg), NMR (300 MHz) ($DMSO_{d6}$, AcOD, TFA): 1.8 (d,3H), 3.6 (m,2H), 4–4.5 (m,2H); 5.1 (d,1H); 5.7 (d,1HO); 6–6.4 (m,1H); 6.8 (s,1H); 6.7–7.3 (m,3H).

PREPARATION OF STARTING MATERIAL

7-Amino-3-[(2-(3,4-dihydroxyphenyl)-1,3,4-thiadiazol-5-ylthiomethyl]ceph-3-em-4-carboxylic acid.

(Starting material for Examples 2 and 3) was prepared as follows:

To a solution of 2-mercapto-5-(3,4-dihydroxyphenyl)-1,3,4-thiadiazole (695 mg) in water (10 ml) and DMF (3 ml) was added NaHCO₃ (1.03 g) followed by 7-amino-3-iodomethylceph-3-em-4-carboxylic acid (1.2 g). Stirring was continued for 2 hours at room temperature. The mixture was acidified to pH 3.5–4 and the title compound (1.1 g) was obtained as a precipitate, which was filtered off and dried. NMR (DMSO$_{d6}$, AcOD, TFAd) 3.75 (m,2H) 4.2–4.6 (m,2H), 5.1 (d,1H); 5.2 (d,1H), 6.85 (d,1H); 7.15 (d,1H); 7.3 (d,1H).

EXAMPLE 4

The process of Example 3 was repeated starting from (Z)-1-(2-aminothiazol-4-yl)butene-1-carboxylic acid (prepared as described in European Patent Application No. 0107138 which comprises about 25% (E)-isomer and about 75% (Z)-isomer) to form the (E)- and (Z)-isomers of 7-(1-(2-aminothiazol-4-yl)-1-(Z)-butenecarboxamido]-3-[(2-3,4-dihydroxyphenyl)-1,3,4-thiadiazol-5-ylthiomethyl]ceph-3-em-4-carboxylic acid. The isomers of the final product were separated using preparative HPLC using ammonium phosphate buffer/MeOH of 40% MeOH increasing to 50% yielding (Z)-isomer (190 mg; 16%) and (E)-isomer (27 mg; 3%) having NMR as follows in DMSO$_{d6}$, AcOD, TFA:

(Z)-isomer (300 MHz):

1.05 (l,3H); 2.25 (m,2H); 3.65 (d,1H); 3.8 (d,1H); 4.25 (d,1H); 4.55 (d,1H); 5.15 (d,1H); 5.75 (d,1H); 6.25 (t,1H); 6.55 (s,1H); 6.85 (d,1H); 7.15 (dd,1H); 7.35 (d,1H).

(E)-isomer (90 MHz):

1.05 (t,3H); 2.2 (m,2H); 3.7 (m,2H); 4.24 (d,1H); 4.52 (d,1H); 5.1 (d,1H); 5.7 (d,1H); 6.7–7.4 (m,5H).

EXAMPLE 5

7-[2-(2-Aminothiazol-4-yl)-2-((Z)-methoxyimino)acetamido]-3-[(6,7-dihydroxyquinazolin-4-yl)thiomethyl]ceph-3-em-4-carboxylic acid.

(a) (1) (5 g) (prepared from the corresponding oxo compound using Lawesson's reagent in acetonitrile) was dissolved in dichloromethane (anhydrous) (75 ml) with the addition of BSA (17 ml). BBr₃ (13 ml) was added to the solution at 0° C. The reaction mixture was stirred at room temperature overnight. The dichloromethane was evaporated and the residue dissolved in MeOH, evaporated, and purified by HP20SS chromatography. The dihydroxy product (2.6 g) was obtained: NMR (DMSO$_{d6}$/TFA); 7.13 (s,1H); 7.92 (s,1H); 8.91 (s,1H).

(b) 7-Aminocephalosporanic acid (1.4 g) in acetonitrile (10 ml) and boron trifluoride ethoxylate (4 ml) was treated with (2) (1 g) at room temperature for 2.5 hours. Acetonitrile was evaporated, the crude reaction mixture poured into water, and the precipitate filtered and dried. A crude product (1.9 g) was obtained, which was purified by chromatography over HP20SS resin, eluting with water containing 1% AcOH, and MeOH at varying proportions. Two cephalosporin derivatives were thus obtained. The more polar derivative (3) (280 mg) eluted at 5% MeOH and the less polar derivative (330 mg) eluted at 10% MeOH (330 mg). NMR (DMSO$_{d6}$, TFA) (more polar derivative): 3.64 (d,1H); 3.88 (d,1H); 4.32 (d,1H); 4.96 (d,1H); 5.2 (s,2H); 7.37 (s,1H); 7.45 (s,1H); 9.11 (s,1H).

(c) The cephalosporins (3) (200 mg), mercaptobenzthiazolyl 2-(2-aminothiazol-4-yl)-2-methoxyiminoacetate (174 mg) and Et₃N (35 μl) in DMF (3 ml) were stirred at room temperature for 2 hours. The solvent was then evaporated and the product purified by chromatography over HP20SS resin, eluting with ammonium carbonate buffer/MeOH using increasing amounts of MeOH. The title compound (39 mg) was obtained, NMR (DMSO$_{d6}$, TFA, AcOH): 3.55 (d,1H) 3.85 (d,1H); 3.95 (s,3H); 4.25 (d,1H); 4.95 (d,1H); 5.15 (d,1H); 5.75 (d,1H); 6.95 (s,1H); 7.35 (s,1H); 7.45 (s,1H); 9.05 (s,1H).

EXAMPLE 6

7-[2-(2-Aminothiazol-4-yl)-2-((Z)-1-carboxy-1-methylethoxyimino)acetamido]-3-[6,7-dihydroxyquinazolin-4-ylthiomethyl]ceph-3-em-4-carboxylic acid.

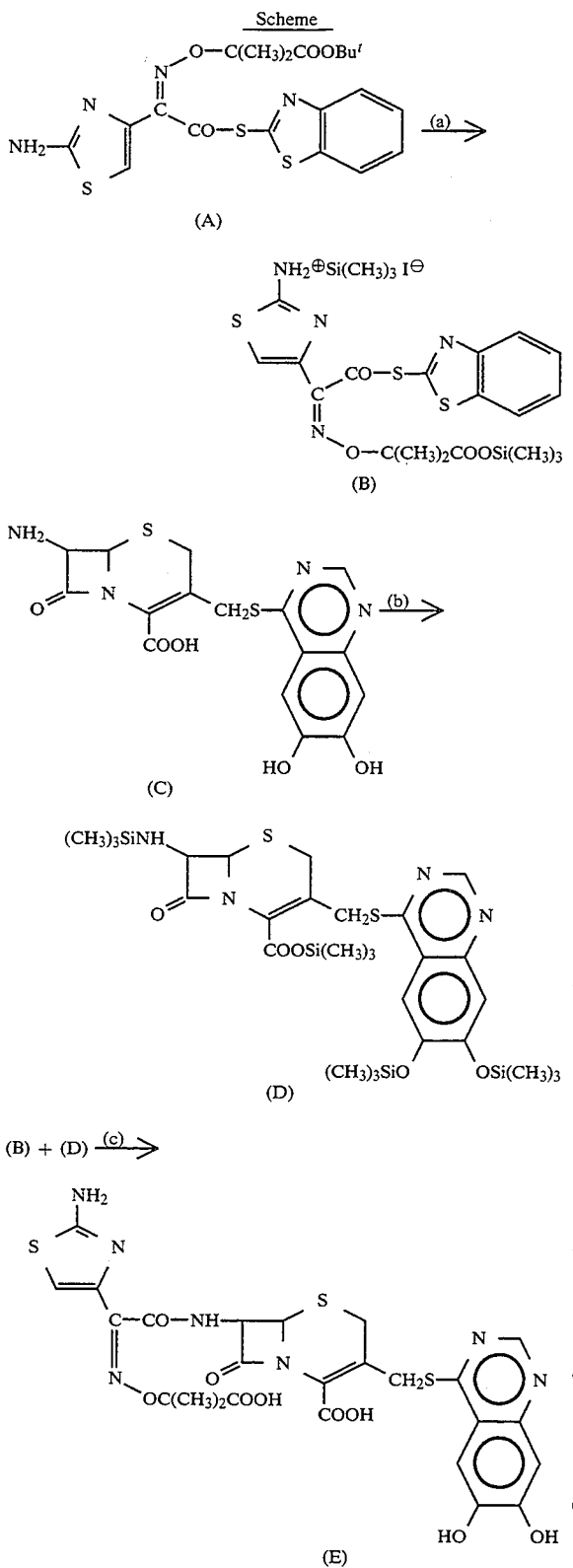

(a) The thioester (A) (400 mg) was dissolved in dichloromethane (2 ml) at room temperature and trimethylsilyl iodide (250 μl) added. The mixture was stirred at room temperature for 4 hours under argon to obtain a solution of the silylated compound (B) in dichloromethane.

(b) Cephalosporin (C) (106 mg) (obtained as in Example 5(b)) in dichloromethane (2 ml) was stirred for one hour at 40° C. under argon with BSA (514 μl) thus forming a solution of the silylated cephalosporin (D) in dichloromethane.

(c) The solution of (D) obtained in (b) was added to the solution of (B) obtained in (a) and stirring was continued for 2 hours at room temperature. The solvents were then evaporated, and the crude product purified by HPLC using ammonium carbonate/MeOH as eluant, with proportions of MeOH varying from 20 to 35%, to yield the title compound (48 mg), NMR (DMSO$_{d6}$, AcOD, TFA): 1.5 (s,6H); 3.52 (d,1H); 3.8 (d,1H); 4.24 (d,1H); 4.92 (d,1H); 5.16 (d,1H); 5.84 (d,1H); 7.0 (s,1H); 7.32 (s,1H); 7.4 (s,1H); 9.04 (s,1H).

EXAMPLE 7

7-[2-(2-Aminothiazol-4-yl)-2-((Z)-methoxyimino)acetamido]-3-[(1-(2-(3,4-dihydroxyphenyl)ethyl)tetrazol-5-yl)thiomethyl]-ceph-3-em-4-carboxylic acid.

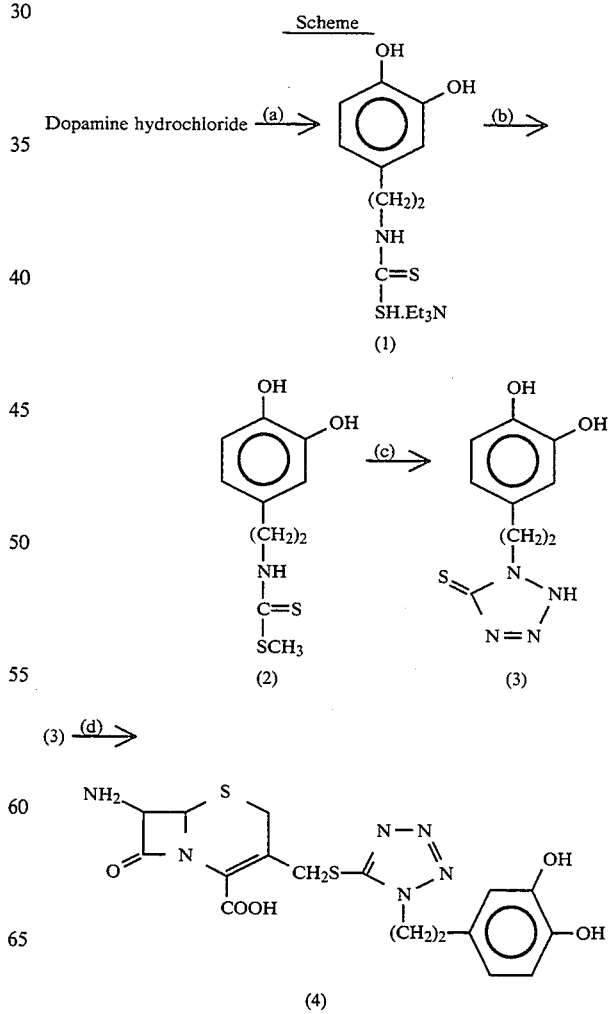

-continued
Scheme

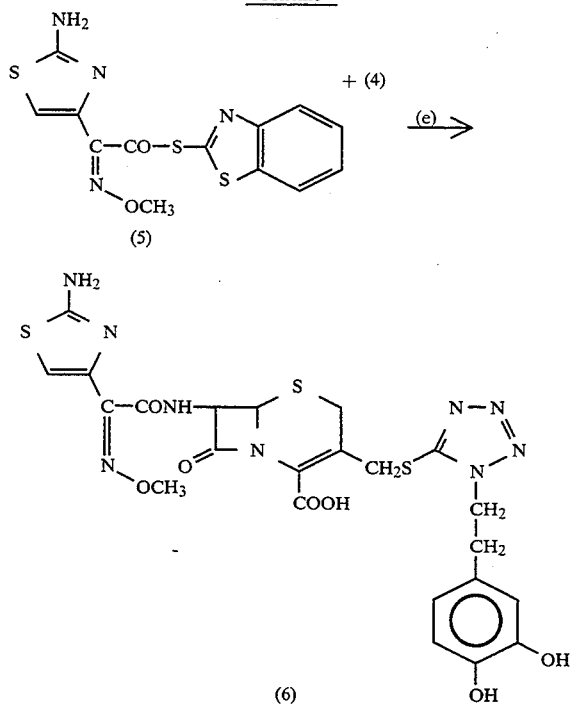

(a) Dopamine hydrochloride (3.8 g) was dissolved in EtOH (40 ml) and Et₃N (4.04 g) added at room temperature followed by CS₂ (1.52 g). The mixture was stirred at room temperature for 2 hrs. until all of the starting material had disappeared (by tlc); to form (1).

(b) Methyl iodide (2.84 g) was added to the product of (a) in solution, stirring for 2 hours at room temperature. The solvents were evaporated, and the crude product purified by silica gel chromtography eluting with dichloromethane/ether to yield the thioester (2) (4.3 g), NMR (DMSO$_{d6}$) 2.5 (s,3H); 2.7 (t,2H); 3.5–3.9 (m,2H); 6.3–6.7 (m,3H); 8.56 (s,1H); 8.68 (s,2H); 9.9 (t,1H).

(c) The thioester (2) (4 g) was dissolved in water (20 ml) and EtOH (20 ml). NaN₃ (1.6 g) was added to the solution, which was then refluxed for 1 hour 45 mins. The solvents were evaporated, and the crude product purified by silica gel chromatography eluting with CH₂Cl₂—MeOH (100→50—50) to obtain compound (3) (1.49 g), NMR (DMSO$_{d6}$): 2.9 (t,2H); 4.3 (t,2H); 6.3–6.7 (m,3H).

(d) Compound (3) (238 mg) was condensed with 7-ACA (272 mg) in CH₃CN (3 ml) with BF₃/Et₂O (1.3 ml) at 40° for 30 mins. The solvents were evaporated and the mixture purified by HP20SS chromatography eluting with MeOH/H₂O using a gradient of MeOH. The cephalosporin (4) was obtained, NMR (DMSO$_{d6}$, ACOD, TFA) 2.94 (t,2H); 3.7 (s,2H); 4.1–4.5 (m,4H); 5.1 (s,2H); 6.2–6.7 (m,3H).

(e) The cephalosporin (4) (120 mg) was dissolved in DMF (3 ml) and Et₃N (26 mg) added, followed by thioester (5) (91 mg). The mixture was stirred at room temperature for 2.5 hours. The solvents were evaporated and the crude product purified using HP20SS chromtography eluting with H₂O/MeOH with a gradient of MeOH to give the title compound (120 mg), NMR (DMSO$_{d6}$, AcOD, TFA): 2.92 (t,2H); 3.52 (d,1H); 3.76 (d,1H); 3.96 (s,3H); 4.1-4.6 (m,4H); 5.1 (d,1H); 5.76 (d,1H); 6.2–7 (m,4H).

EXAMPLE 8

7-[2-(2-Aminothiazol-4-yl)1-2-((Z)-1-carboxy-1-methylethoxyimino)acetamido]-3-[1-(2-carboxy-2-(3,4-dihydroxyphenyl)ethyl)tetrazol-5-ylthiomethyl]-ceph-3-em-4-carboxylic acid.

Scheme

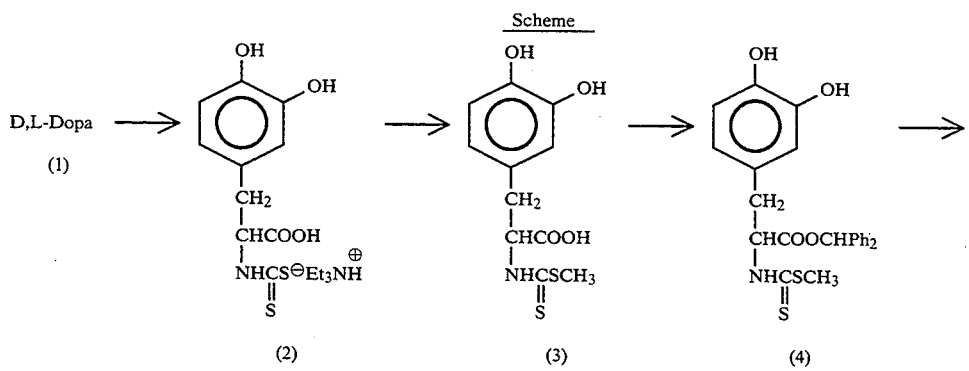

-continued
Scheme

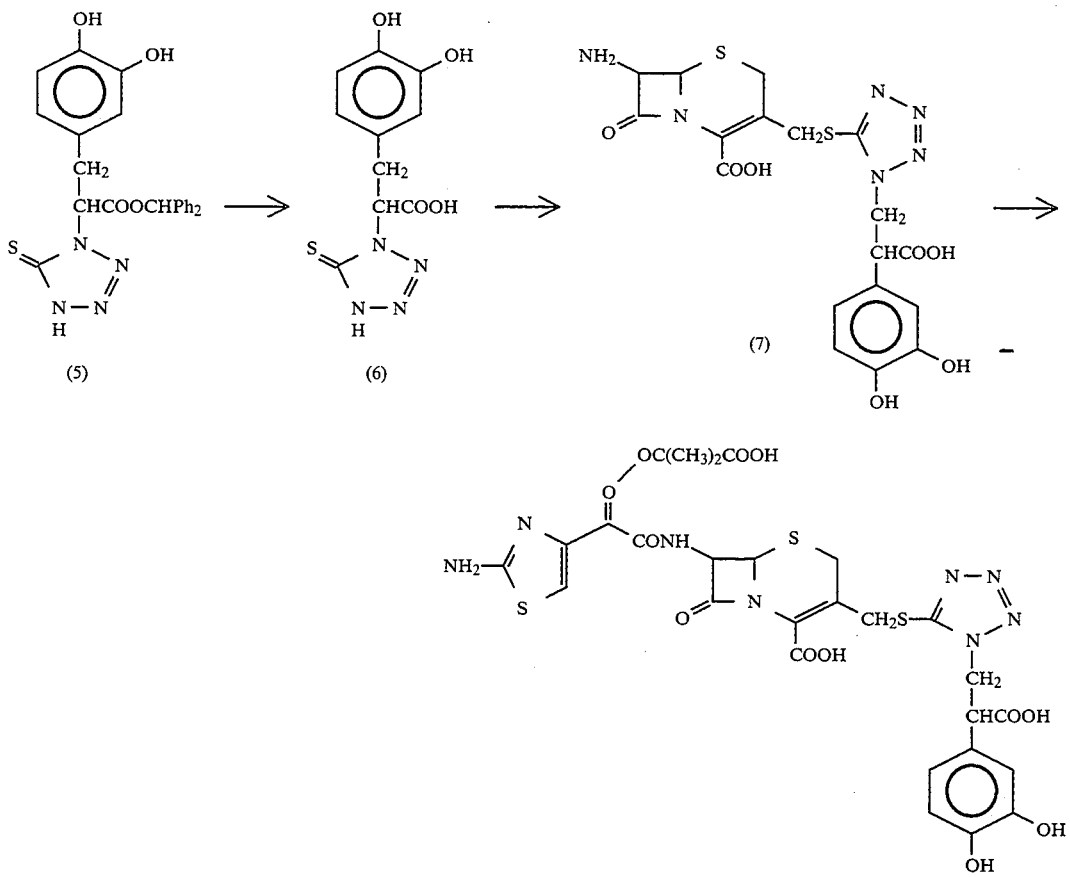

a) To a suspension of D,L-Dopa (5 g) in ethanol (50 ml) was added triethylamine (7 ml), followed by CS$_2$ (1.5 ml). The mixture was stirred at room temperature for 2 hours, water (20 ml) was added and stirring was continued for a further 12 hours. Methyliodide (1.55 ml) was added, the mixture was stirred for a further 2 hours, the solvents were evaporated and the mixture was subjected to chromatography on silica eluting with CH$_2$Cl$_2$/CH$_3$OH (100:0→70:30) to give the thioester (3) (6.26 g), NMR (DMSO-d$_6$/TFAd) 2.53 (s,3H); 3.14 (d,2H); 5.1 (t,1H); 6.4–6.8 (m,3H).

b) To the thioester (3) (3.54 g) in methanol (80 ml) and acetonitrile (80 ml) was added p-toluenesulphonic acid (1.25 g) and then, slowly, was added an excess of diazodiphenylmethane. This mixture was stirred at 40° C. for 3 hours and at room temperature for a further 16 hours. The solvents were evaporated, the mixture dissolved in dichloromethane and purified by chromatography over silica eluting with CH$_2$Cl$_2$/CH$_3$OH (100:0→90:10) to give the ester (4) (2.8 g), NMR (CDCl$_3$) 2.59 (s,3H); 3.10–3.3 (m,2H); 4.7–5.2 (m,1H); 6.13 (d,1H); 6.29 (dd,1H); 6.56 (d,1H); 6.93 (s,1H); 7.31 (2s,1OH).

c) To the ester (4) (2.66 g) in ethanol (10 ml) was added sodium azide (565 mg) in water (5 ml) at room temperature. The mixture was stirred under reflux for 1 hour, the solvents were evaporated and the residue purified by chromatography over silica eluting with CH$_2$Cl$_2$/CH$_3$OH (100:0→60:40) to give compound (5) (1.5 g), NMR (DMSO-d$_6$) 3.41 (d,2H); 5.80 (t,1H); 6.46, 6.54, 6.61 (3s,3H); 6.8 (s,1H); 7.31 (s,1OH).

d) The compound (5) (830 mg) was dissolved in trifluoroacetic acid/anisole at room temperature. After 40 minutes the solvents were evaporated and the crude acid (6) was obtained. This acid (6) (518 mg) and 7-ACA (489 mg) were suspended in acetonitrile (6 ml) and BF$_3$Et$_2$O (2.4 ml) was added with stirring. The mixture was stirred for 35 minutes at 40° C., the solvents were evaporated, and the residue was triturated under ether to give a solid which was purified on HP20SS resin eluting with H$_2$O/CH$_3$OH (100:0→90:10) to give the cephalosporin (7) (497 mg), NMR (DMSO-d$_6$/CD$_3$COOD) 3.3 (d,2H); 3.67 (s,2H); 4.16, 4.48 (2d,2H); 5.13 (s,2H); 5.48 (t,1H); 6.2–6.6 (m,3H).

e) To the cephalosporin (7) (165 mg) in DMF (4 ml) was added triethylamine (46 μl) and compound A (159 mg) (as pictured in Example 6). The mixture was stirred at room temperature for 2.5 hours, the solvents were evaporated and the residue was treated with TFA (4 ml) at room temperature for 1 hour. TFA was evaporated and the residue purified by HPLC eluting with H$_2$O/AcOH/CH$_3$OH (80:1:20→65:1:35) to give the title compound (111 mg), NMR (DMSO-d$_6$/CD$_3$COOD/TFA-d) 1.53 (s,6H); 3.38 (d,2H); 3.6 (s,2H); 4.16–4.18 (2d,2H); 5.12 (d,1H); 5.84 (d,1H); 5.5 (t,1H); 6.2–6.7 (m,3H); 7.04 (s,1H).

EXAMPLE 9

7-[2-(2-Aminothiazol-4-yl)-2-((Z)-carboxy-1-methylethoxyimino)acetamido]-3-[(1-(2-carboxymethyl-4,5-dihydroxyphenyl)tetrazol-5-yl)thiomethyl]-ceph-3-em-4-carboxylic acid.

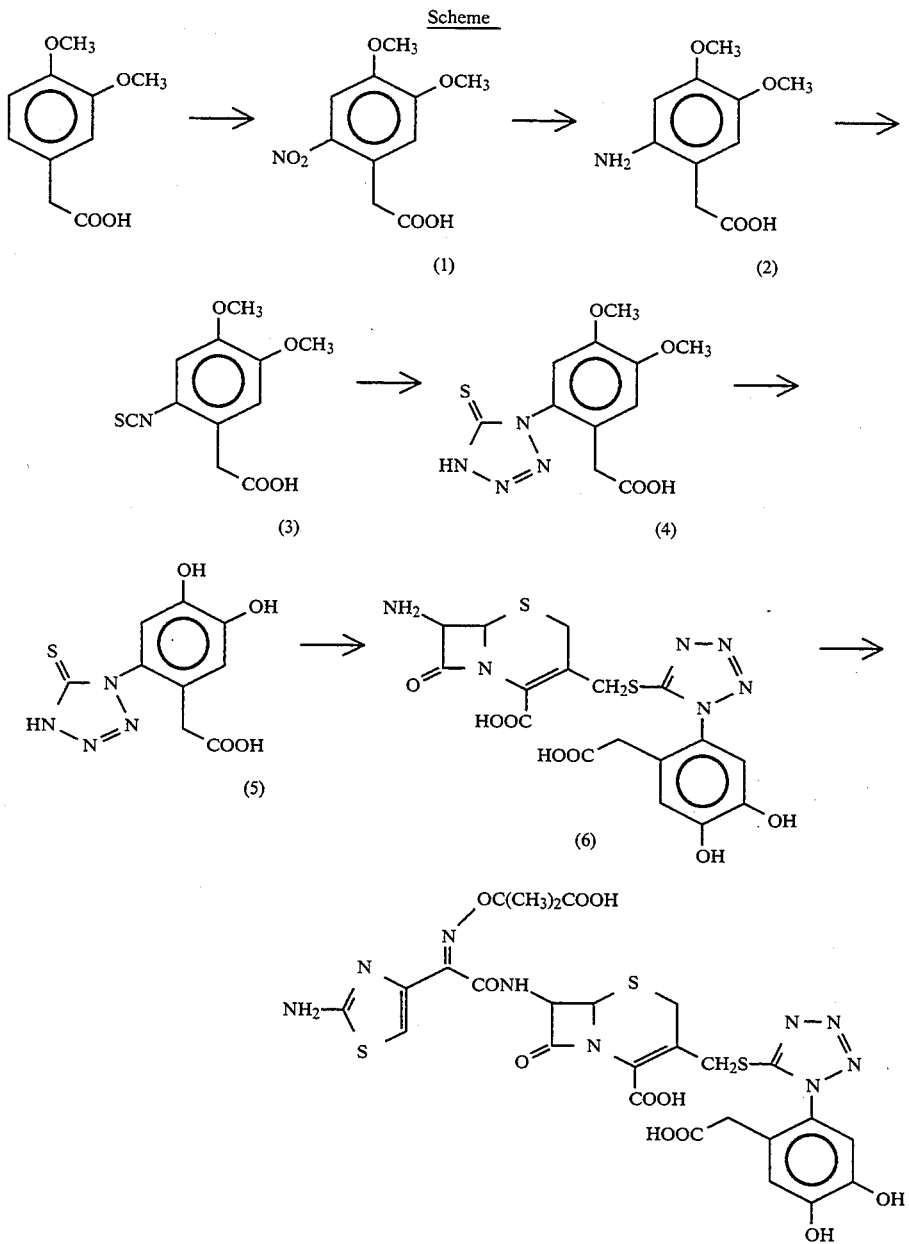

Scheme a) 3,4-Dimethoxyphenylacetic acid (7.84 g) was solubilised in ether (100 ml) and AcOH (20 ml). Fuming HNO$_3$ (1.68 ml) was added to the solution dropwise. Stirring was maintained at room temperature for 16 hours. The precipitate was filtered, washed with ether and dried to give compound (1) (4.19 g), NMR (DMSO-d$_6$) 3.88 (s,3H); 3.80 (s,3H); 3.97 (s,2H); 7.15 (s,1H); 7.70 (s,1H).

b) Compound (1) (4.19 g) was solubilised in methanol (200 ml) and TFA (2 ml). 10% Pd/C (200 mg) was added and the mixture was hydrogenated at room temperature and atmospheric pressure for 2 hours. The catalyst was filtered off and the solvents evaporated to give (2) as a crude residue.

c) Compound (2) (3.6 g) was solubilised in actonitrile (35 ml) and water (35 ml) in the presence of triethylamine (3.6 ml). The mixture was cooled to 0° C. in an ice-bath, thiophosgene (1.6 ml) was added dropwise and after a few minutes the mixture was acidified with 2N HCL and extracted into ether to give isothiocyanate (3) (2.3 g). This was dissolved in ethanol (60 ml) and water (30 ml) containing sodium bicarbonate (830 mg). An aqueous solution of sodium azide (897 mg) in water (30 ml) was added, the mixture was maintained at 40° C. for 3½ hours, cooled, acidified with 2N HCl, evaporated and the residue was purified by HP20SS chromatography, eluting with H$_2$O/AcOH (100:1:0→25:1:75) to give compound (4) (960 mg), NMR (DMSO-d$_6$) 3.51 (s,3H); 3.78, 3.86 (2s,6H); 7.12 (s,2H).

d) To compound (4) (900 mg) in dichloromethane (50 ml) was added BSA (1.5 ml). The solution was cooled to 0° C. and BBr3 (2 ml) added with stirring for 3½ hours. The solvents were evaporated and the residue hydrolysed by pouring into water at 0° C. The resultant reaction mixture was purified by chromatography on HP20SS resin eluting with H2O/AcOH/CH3OH (100:1:0→80:1:20) to give the dihydroxy compound (5) (700 mg), NMR 3.33 (s,2H); 6.79, 6.87 (2s,2H).

e) To dihydroxy compound (5) (650 mg) and 7-ACA (655 mg) in acetonitrile (25 ml) was added BF3.Et2O (4 ml) at room temperature with stirring. After stirring at 40° C. for 30 minutes the solvent was evaporated and the residue triturated under ether and purified by HP20SS resin chromatography eluting with H2O/AcOH/CH3OH (100:1:0→ 80:1:20) to give the cephalosporin (6) (622 mg), NMR (DMSO-d6/TFAd) 3.22 (s,2H); 3.80 (s,2H); 4.28 (d,1H); 5.19 (s,2H); 6.81, 6.92 (2s,2H).

f) To cephalosporin (6) (160 mg) in DMF (4 ml) was added triethylamine (46 μl) and Compound A (159 mg) (as pictured in Example 6). The mixture was stirred for 4 hours at room temperature, the solvents were evaporated and the residue dissolved in TFA (4 ml) and stirred for 2½ hours. The TFA was evaporated and the residue purified by HP20SS resin chromatorgraphy eluting with H2O/AcOH/CH3OH (100:1:0→40:1:60) to give the title compound (120 mg), NMR (DMSO-d6/TFAd) 1.53 (s,6H); 3.21 (s,2H); 3.70 (s,2H); 4.20 (d,1H); 4.60 (d,1H); 5.16 (d,1H); 5.83 (d,1H); 6.78, 6.90 (2s,2H); 7.05 (s,1H).

EXAMPLE 10

7-[2-(2-Aminothiazol-4-yl)-2-((Z)-1-carboxy-1-methylethoxyimino)acetamido-3-[(1-(2-(3,4-dihydroxyphenyl)ethyl)tetrazol-5-yl)thiomethyl]ceph-3-em-4-carboxylic acid.

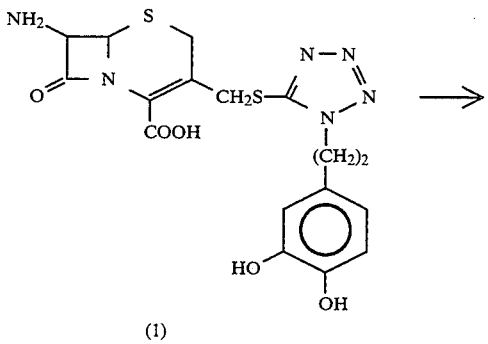

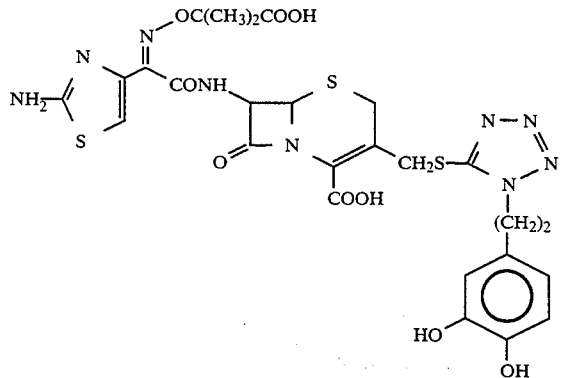

To cephalosporin (1) (135 mg) (see Example 7) in solution in DMF, was added Et3N (42 μl) followed by Compound A (174 mg) (as depicted in Example 6), at room temperature. Stirring was continued for 2½ hours, the solvent was evaporated, the residue was dissolved in TFA (3 ml) and stirred at room temperature for 1 hour. The solvent was evaporated and the residue chromatographed over HP20SS resin eluting with H2O/AcOH/CH2OH (45.1:55) to give the title compound (98 mg) NMR (DMSOd6, CD3COD, TFAd) 1.55 (s,6H); 2.95 (t,2H); 3.5–3.8 (m,2H); 4.1–4.6(m,4H); 5.15, 6.85 (2d,2H); 6.2–6.7 (m,3H); 7.05 (s,1H).

We claim:

1. A compound of the formula (XVI):

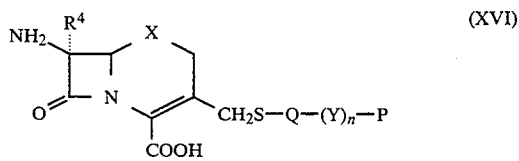

wherein:

X is sulphur or sulphinyl;

R4 is hydrogen, methoxy or formamido;

wherein —S—Q— is of the formula (VIII):

which optionally may bear a positive charge, and which optionally may be substituted on an available nitrogen atom by carboxy, sulpho, $C_{1-4}$ alkoxycarbonyl or $C_{1-4}$ alkyl (which alkyl group may itself optionally be substituted by carboxy, sulpho or $C_{1-4}$ alkoxycarbonyl);

P represents:

(i) a benzene ring (optionally fused to a further benzene ring (so forming a naphthyl group) or to a 5 or 6 membered heterocyclic aromatic group containing 1, 2 or 3 heteroatoms selected from nitrogen, oxygen and sulphur) said benzene ring (or in the case of naphthyl either benzene ring) substituted by groups $R^1$ and $R^2$ which are ortho with respect to one another wherein $R^1$ is hydroxy or an in vivo hydrolysable ester thereof and $R^2$ is hydroxy, an in vivo hydrolysable ester thereof, carboxy, sulpho, hydroxymethyl, methanesulphonamido or ureido;

(ii) a group of the formula (II):

or, (iii) a group of the formula (III):

wherein M is oxygen or a group $NR^3$;

wherein $R^3$ is hydrogen or $C_{1-4}$ alkyl:

ring P (or, in the case wherein ring P is a benzene ring and is fused to another benzene ring, either benzene ring) is optionally further substituted by $C_{1-4}$ alkyl, halo, hydroxy, hydroxy $C_{1-4}$ alkyl, cyano trifluoromethyl, nitro, amino, $C_{1-4}$ alkylamino, di-$C_{1-4}$ alkylamino, amino $C_{1-4}$ alkyl, $C_{1-4}$ alkylamino $C_{1-4}$ alkyl, di-$C_{1-4}$ alkylamino $C_{1-4}$ alkyl, $C_{1-4}$ alkanoyl, $C_{1-4}$ alkoxy, $C_{1-4}$ alkylthio, $C_{1-4}$ alkanoyloxy, carbamoyl, $C_{1-4}$ alkylcarbamoyl, di-$C_{1-4}$ alkyl carbamoyl, carboxy, carboxy $C_{1-4}$ alkyl, sulpho, sulpho $C_{1-4}$ alkyl, $C_{1-4}$ alkanesulphonamido, $C_{1-4}$ alkoxycarbonyl, $C_{1-4}$ alkanoylamino, nitroso, thioureido, amidino, ammonium, mono-, di- or tri-$C_{1-4}$ alkylammonium pyridinium, or a 5-membered heterocyclic ring containing 1 to 4 heteroatoms selected from oxygen, nitrogen and sulphur which is optionally substituted by 1, 2 or 3 $C_{1-4}$ alkyl or $C_{1-4}$ alkoxy groups, $n=0$ or 1 such that when $n=1$ Y represents a covalent bond between Q and P or a (1-4C)alkylene group optionally substituted by carboxy or sulpho or Y represents a group $-(CH_2)_m-Y'-$ wherein $m=1$ or 2 and Y' is $-O.CO-$ or $-NH.CO-$; and when $n=0$ Q and P both represent monocyclic rings which are fused on an available carbon—carbon or carbon—nitrogen bond.

2. A compound according to claim 1 wherein P is a benzene ring substituted by groups $R^1$ and $R^2$ which are ortho to one another wherein $R^1$ and $R^2$ are independently hydroxy or an in vivo hydrolysable ester thereof said benzene ring being optionally further substituted.

3. A compound according to claim 1 wherein $-(Y)_n-$ represents a covalent bond between groups Q and P.

4. A compound according to claim 1 wherein $-(Y)_n-$ is methylene or ethylene.

* * * * *